US00PP09492P

United States Patent [19]

Zary

[11] Patent Number: Plant 9,492

[45] Date of Patent: Apr. 2, 1996

[54] CLIMBER ROSE PLANT NAMED 'JACPICL'

[75] Inventor: Keith W. Zary, Thousand Oaks, Calif.

[73] Assignee: Bear Creek Gardens, Inc., Medford, Oreg.

[21] Appl. No.: 386,145

[22] Filed: Feb. 8, 1995

[51] Int. Cl.[6] ..... A01H 5/00

[52] U.S. Cl. ..... Plt./5

[58] Field of Search ..... Plt./1, 5, 26

*Primary Examiner*—Howard J. Locker

*Attorney, Agent, or Firm*—Klarquist Sparkman Campbell Leigh & Whinston

[57] ABSTRACT

A climber rose plant characterized by the unique combination of its strong, upright then arching habit of growth, its ability to have buds break freely along its arching stems, producing an abundance of bloom, by its dark green, glossy, disease-resistant foliage, and its production of flowers in clusters of 3 to 9.

2 Drawing Sheets

The present invention relates to a new and distinct variety of rose plant of the climber class which was originated by me by crossing the variety JACship, U.S. Plant Pat. No. 7,948, with the variety INTERlada, U.S. Plant Pat. No. 6,068.

The primary objective of this breeding was to produce a new rose variety having the fully double pink flowers and profuse flowering of the female parent combined with the long arching canes and good disease resistance of the male parent. The objective was substantially achieved, along with other desirable improvements, as evidenced by the following unique combination of characteristics that are outstanding in the new variety and that distinguish it from its parents, as well as from all other varieties of which I am aware:

1. A strong, vigorous, upright then arching growth habit;
2. Breaks freely along the stem producing continuous bloom;
3. Dark green, glossy, disease-resistant foliage; and
4. Flowers produced in clusters of 3 to 9.

Asexual reproduction of this new variety by budding, as performed at Wasco, Calif., shows that the foregoing and all other characteristics and distinctions come true to form and are established and transmitted through succeeding propagations.

The accompanying illustrations show typical specimens of the vegetative growth and flowers of this new variety in different stages of development, depicted in color as nearly true as it is reasonably possible to make the same in a color illustration of this character.

Sheet 1 shows shows the whole plant growing in the field.

Sheet 2 provides a more detailed view of the vegetative growth and flowers of the new variety.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—JACship, U.S. Plant Pat. No. 7,948.

*Pollen parent.*—INTERlada, U.S. Plant Pat. No. 6,068.

Classifications:

*Botanical.*—*Rosa hybrida.*

*Commercial.*—Climber.

FLOWER

Observations made from specimens grown in a garden environment of Somis, Calif., in March through October, 1994.

Blooming habit: Continuous

Bud:

*Size.*—1 to 1½ inches long when the petals start to unfurl.

*Form.*—The bud form is long, pointed ovoid.

*Color.*—When sepals first divide, bud color is Red Group 38B with a strong yellow tone at the base of the flower petals. When half blown, the upper and lower sides of the petals are Red Group 38B.

*Sepals.*—Color: Green Group 138C. Surface texture: Covered in fine hairs. There are three lightly appendaged sepals with many glands on sepal edges. There are two unappendaged sepals with hairy edges.

*Receptacle.*—Color: Green Group 141C. Shape: Apple. Size: Small (¼ inch by ¼ inch). Surface: Glandular.

*Peduncle.*—Length: Short (1½ inches to 2 inches). Surface: Glandular. Color: Bronzy. Strength: Stiff, bending, slender.

Bloom:

*Size.*—Medium. Average open size is 3 inches to 3½ inches.

*Borne.*—Several together in rounded clusters of 3 to 9 flowers.

*Stems.*—Strong, long (up to 4 feet).

*Form.*—When first open: High centered. Permanence: Flattens, outer petals curl back.

*Petalage.*—Number of petals under normal conditions: 25 to 30.

*Color.*—The upper side of the petals is Red Group 38B. The reverse side of the petals is Red Group 38B. The base of each petal has a bright yellow (Yellow Group 4A, ⅜ inch by ⅜ inch) half moon at the point of attachment. The major color on the upper side is Red Group 38B.

*Variegations.*—None.

*Discoloration.*—The general tonality at the end of the first day: No change. At the end of the third day: No change.

*Fragrance.*—Moderate.

Petals:

*Texture.*—Thick, leathery.

*Shape.*—Deltoid.

*Form.*—Tips slightly recurved.

*Arrangement.*—Imbricated, with few petaloids in the center.

*Persistence.*—Drop off cleanly.

*Lastingness.*—On the plant: Fair (4 to 5 days). As a cut flower: Not tested.

Reproductive parts:

*Anthers.*—Size: Large. Quantity: Many. Color: Yellow. Arrangement: Regular around styles.

*Filaments.*—Color: Reddish.

*Pollen.*—Color: Gold Yellow.
*Styles.*—Yellowish white.
*Stigmas.*—Color: Greenish white.
Form: Climber.
Growth: Very vigorous; upright then arching and branching.
Foliage:
*Number of leaflets of normal mid-stem leaves.*— 5 or 7.
*Size.*—Medium (5 inches by 4 inches).
*Quantity.*—Abundant.
*Color.*—New foliage: Greyed-Purple 183A upper and lower surface. Old foliage: Upper surface: Green Group 137A. Lower surface: Green Group 137C.
Leaflets:
*Shape.*—Pointed oval.
*Texture.*—Upper side: Leathery, glossy.
*Edge.*—Serrated.
*Serration.*—Single, small.
*Petiole rachis.*—Color: Reddish.
*Petiole underside.*—Smooth with occasional prickles.
*Stipules.*—Medium (½ inch to ¾ inch); bearded.
*Disease resistance.*—Resistant to mildew and rust under normal growing conditions at Somis, Calif.
Wood:
*New wood.*—Color: Reddish but turns green very quickly. Bark: Smooth.
*Old wood.*—Color: Green. Bark: Smooth.
Prickles:
*Quantity.*—On main canes from base: ordinary. On laterals from main canes: Ordinary.
*Form.*—Medium (¼ inch), hooked downward.
*Color when young.*—Red.
Small prickles:
*Quantity.*—On main stalks: None. On laterals: None.

I claim:

1. A new and distinct variety of rose plant of the climber class, substantially as herein shown and described, characterized particularly as to novelty by the unique combination of its strong, upright then arching habit of growth, its ability to have buds break freely along its arching stems, producing an abundance of bloom, by its dark green, glossy, disease-resistant foliage, and its production of flowers in clusters of 3 to 9.

* * * * *

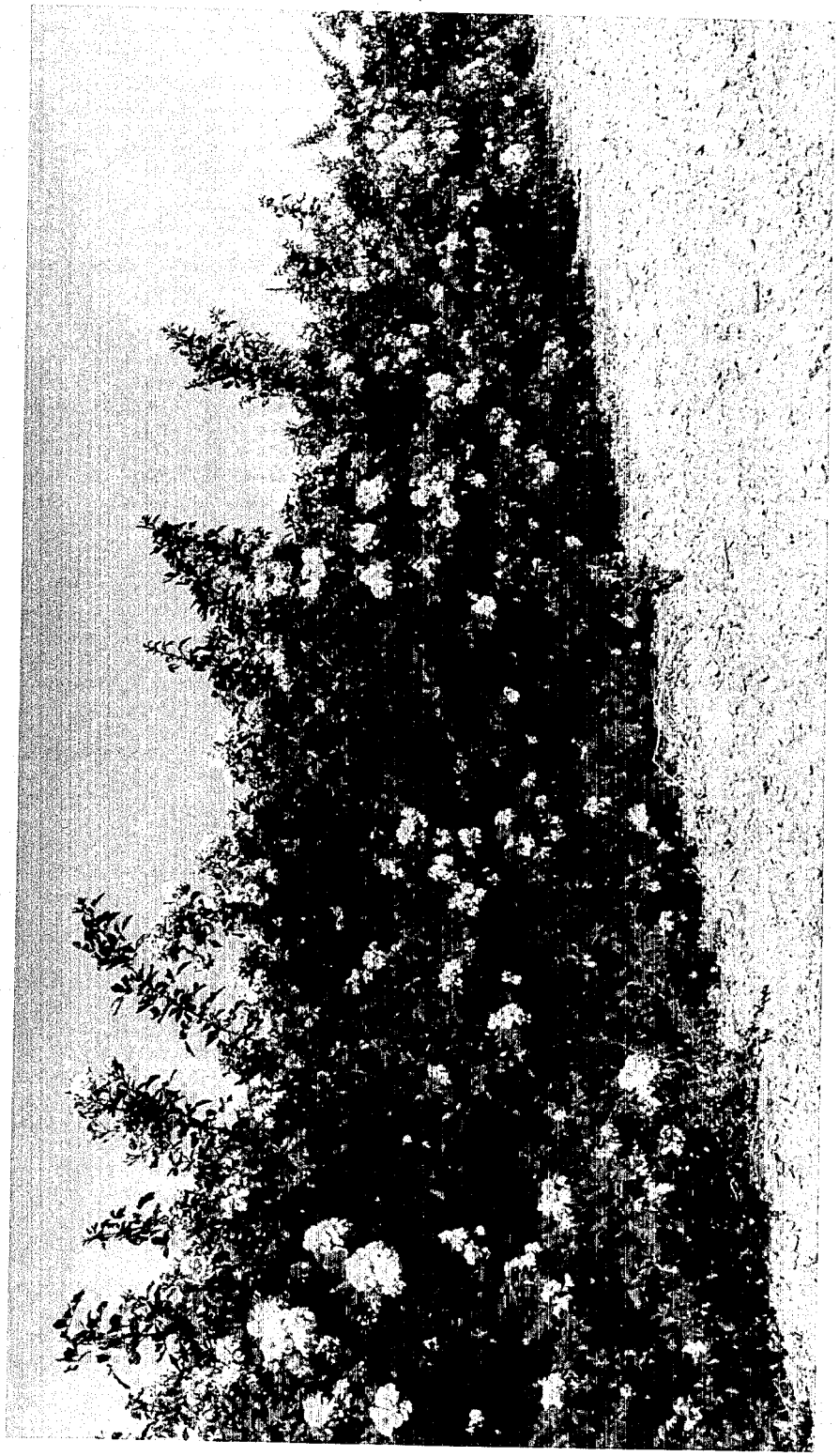

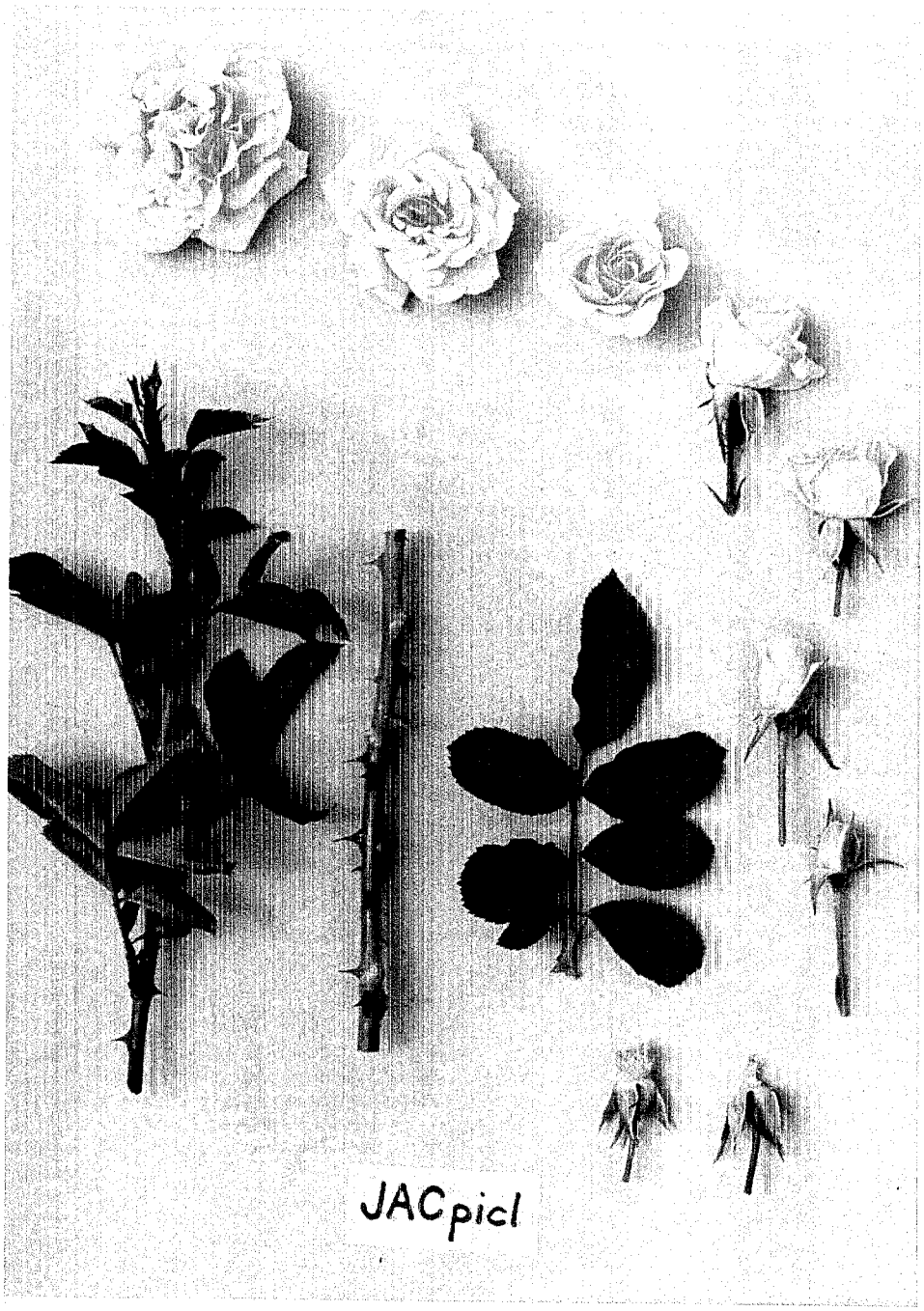
JACpicl